United States Patent
Olsen

[11] Patent Number: 6,071,356
[45] Date of Patent: *Jun. 6, 2000

[54] CLEANING-IN-PLACE WITH A SOLUTION CONTAINING A PROTEASE AND A LIPASE

[75] Inventor: Hans Sejr Olsen, Holte, Denmark

[73] Assignee: Novo Nordisk Als, Bagsvaerd, Denmark

[ * ] Notice: This patent issued on a continued prosecution application filed under 37 CFR 1.53(d), and is subject to the twenty year patent term provisions of 35 U.S.C. 154(a)(2).

[21] Appl. No.: 09/003,768

[22] Filed: Jan. 7, 1998

Related U.S. Application Data

[63] Continuation of application No. PCT/DK96/00301, Jul. 3, 1996.

[30] Foreign Application Priority Data

Jul. 12, 1995 [DK] Denmark .................................. 0819/95
Nov. 2, 1995 [DK] Denmark .................................. 1221/95

[51] Int. Cl.[7] .......................... C11D 3/386; C11D 17/00; B08B 9/20
[52] U.S. Cl. .................................. 134/26; 134/27; 134/28; 134/29; 510/111; 510/218; 510/234; 510/392; 510/530
[58] Field of Search ................................ 516/111, 218, 516/234, 397, 530; 134/26–29

[56] References Cited

U.S. PATENT DOCUMENTS

| | | | |
|---|---|---|---|
| 4,212,761 | 7/1980 | Ciaccio | 252/174.12 |
| 4,243,543 | 1/1981 | Gilbert et al. | 252/105 |
| 4,456,544 | 6/1984 | Lupova et al. | 252/171.12 |
| 5,064,561 | 11/1991 | Roullard | 252/174.12 |
| 5,156,761 | 10/1992 | Aaslyng et al. | 252/174.12 |
| 5,571,446 | 11/1996 | Rouillard | 510/234 |
| 5,783,542 | 7/1998 | Rouillard | 510/234 |
| 5,858,117 | 1/1999 | Oakes et al. | 134/27 |
| 5,858,941 | 1/1999 | Oaks et al. | 510/179 |
| 5,861,366 | 7/1998 | Ihns et al. | 510/320 |

FOREIGN PATENT DOCUMENTS

| | | |
|---|---|---|
| 61 75 85 | 8/1935 | WIPO . |
| WO 93/05187 | 3/1993 | WIPO . |
| WO 92/03529 | 6/1994 | WIPO . |
| WO 94/23004 | 10/1994 | WIPO . |

OTHER PUBLICATIONS

Mejeriprodukter, Hygien, Livsmedelsbranchernas yrknesnamnd, Brevskolan, pp. 1–32 (1980).
Sprenger, Hygiene of Management, p. 135.

*Primary Examiner*—Kery Fries
*Attorney, Agent, or Firm*—Steve T. Zelson; Valeta Gress

[57] ABSTRACT

The present invention relates to methods of cleaning-in-place soiled process equipment comprising circulating a solution comprising a protease and a lipase for a sufficient period of time to permit action of the enzymes.

12 Claims, No Drawings

CLEANING-IN-PLACE WITH A SOLUTION CONTAINING A PROTEASE AND A LIPASE

CROSS-REFERENCE TO RELATED APPLICATIONS

This application is a continuation of PCT/DK96/00301 filed on Jul. 3, 1996 and claims priority under 35 U.S.C. 119 of Danish application serial nos. 0819/95 and 1221/95 filed Jul. 12, 1995 and Nov. 2, 1995, respectively, the contents of which are fully incorporated herein by reference.

FIELD OF INVENTION

This invention relates to an enzymatic method of cleaning-in-place soiled process equipment, in particular dairy and slaughter house process equipment.

BACKGROUND OF THE INVENTION

Cleaning-in-place (CIP), which has replaced hand cleaning in, e.g., dairies, breweries and all potable liquid installations, involves circulating non-foaming or low foaming detergents through process equipment in the assembled state.

A typical basic CIP sequence may consist of the following five stages (for reference see "Hygiene for Management" by Richard A. Sprenger, 5th Ed., p. 135, published by Highfield Publications):
(1) pre-rinse with cold water to remove gross soil;
(2) detergent circulation to remove residual adhering debris and scale;
(3) intermediate rinse with cold water to remove all traces of detergent;
(4) disinfectant circulation to destroy remaining microorganisms;
(5) final rinse with cold water to remove all traces of disinfectants.

The time allowed for each operation must be determined for each particular plant or circuit being cleaned.

The detergent in step (2) in the above mentioned sequence is often 0.5–1% NaOH/KOH (+/− surfactants) at 75–85° C. followed by a rinsing with water followed by a treatment with 0.5–1% $HNO_3$ (+/− surfactants) at 10–50° C. The surfactants used are typically selected from nonionic and/or anionic surfactants often in combination with sequestering agents.

The industry wants more gentle cleaning media than the ones described above; a new cleaning media should offer one or more of the following advantages: Reduction of the water consumption, less damage to the equipment, lower temperatures, less risk for residues of surfactants and/or caustic and/or acids and/or sequestering agents in the food or beverage, less risk for accidents to the people handling the cleaning media. For membrane cleaning media also an improved cleaning efficacy is wanted.

SUMMARY OF THE INVENTION

In this invention it is surprisingly found that a solution comprising a protease and a lipase is very efficient in cleaning, e.g., process equipment containing residues of milk or burnt milk.

Accordingly, the present invention relates to a method of cleaning-in-place soiled process equipment comprising circulating a solution comprising a protease and a lipase for a sufficient period of time to permit action of the enzymes.

DETAILED DISCLOSURE OF THE INVENTION

The method of the present invention may be applied to cleaning-in-place of any process equipment known in industry.

The method is particularly well suited for cleaning process equipment that prior to cleaning has contained materials containing proteins, fats or carbohydrates, in particular materials that prior to cleaning has contained fats and proteins such as milk, whey, cheese, cream, butter, milk based desserts, fermented milk products such as yoghurt, ymer, Gaio, meat, meat emulsions, sausages, whole meat cuts, feed products, liquid feed products, soy milk, tofu, fermented oriental fat-containing foods, extruded foods such as spaghetti and egg products, mayonnaise, sauces such as bearnaise sauce, fish, fish emulsions, fish sausages and whole fish cuts.

The mechanism of the enzymatic cleaning of the hard surfaces of the process equipment is believed to be the following:

During enzymatic degradation of the soils (protein, fat, carbohydrates) a solubilization occur. Using a protease, the sections formed by the degradation of the protein become soluble. Using a lipase, the degraded fat becomes soluble at alkaline conditions. Using a carbohydrase, degraded polysaccharides becomes soluble or the viscosity may be reduced significantly which help on the mechanical action needed for effective cleaning and rinsing.

Proteins are degraded to emulsifying or foaming products. When degraded by use of efficient serine proteases the amphophilic properties of the peptides formed secure a high foam or emulsification effect. The peptides so formed also have a significant buffer capacity, and generally stabilize enzymes in solution.

Fats degraded by use of a lipase under alkaline conditions form soaps or other amphipatic compounds. Using a 1.3 specific lipase monoglycerides are formed, which are known to be good emulsifiers.

When sufficient soil material is present for production of the above mentioned materials no, or very little amounts of surfactants, other than those produced in situ during the cleaning is necessary, because the enzymes form soap and emulsifier from the degraded soil.

The following advantages with use of enzymes compared to traditional cleaning agents can be mentioned:
In situ production of soap, emulsifiers, stabilizers due to the degradation of the soils.
Easier to rinse away.
Biodegradable waste products.
Low foaming (especially an advantage in CIP, and particularly within membrane cleaning).
Anticorrosive to metals and synthetic polymers used for membranes, sealings and tubes.
Longer lifetime is found.
The time for cleaning may be reduced.
The energy consumption may be reduced. (The enzymatic cleaning is performed at a lower temperature).
The cleaning may be more efficient.
A possibility for phosphate free cleaning processes.
The waste water treatment may be cheaper.
The waste water may be used for feed or food.
The waste water may also be used for other purposes like emulsifiers, buffers or cleaning agents for reuse or use in other places, such as lubrication purposes or polymer production.

The enzymatic cleaning according to the invention is effective, i.e. the substrate for the microorganisms (=the soil) is so effectively removed that growing of microbial cells is limited and/or inhibited. This is a very important feature, in particular in the slaughter house and in the dairy industries, where the microbial control is very strict.

The method of the invention could therefore be very important in e.g. cleaning milking machines because it is a problem today to keep the inner surfaces of the milking machines free of microorganisms.

As demonstrated in the enclosed examples the method of the invention works very well without any detergents being added. It may, however, in some cases be an advantage also to add a small amount of a surfactant, preferably a non-ionic surfactant, in an amount of up to 1% w/w, preferably in an amount of up to 0.1% w/w, more preferably in an amount of up to 0.025% w/w. Hereby, in some cases, an even better cleaning effect can be obtained, or the amount of enzymes can be reduced, or the cleaning time can be reduced.

Surfactants

If a surfactant is used it will normally be selected from the nonionic group or from the amphoterics. One or more of the following nonionic surfactants may be applied:
glycerol derivatives,
sorbitan, glucose, sucrose derivatives,
fatty acid ethoxylates,
fatty acid ethoxylates propoxylates,
fatty alcohol ethoxylates,
alkyl phenol ethoxylates,
fatty alcohol ethoxylates propoxylates,
fatty esters of polyalcohol ethoxylates,
end-blocked ethoxylates,
polypropylene glycols,
polyethylene glycols.

Among the amphoterics one or more of following may be applied:
alkylimidazoline,
alkylbetaines,
alkylamidobetaines,
protein derivatives.

Process Equipment

According to the invention any process equipment known in the art may be cleaned as described herein. In particular, all process equipment used in the food/feed industry may advantageously be cleaned as described in the present invention.

Also process equipment used for waste treatment, e.g., oil/water separators, tanks, pipes, and membrane separation equipment on, e.g., shipboard installations, in particular process equipment for the treatment of the so called "Gray water", may be cleaned as described in the present invention.

Dairy, slaughter house, brewery, feed, feed pelleting, fish and fish meal process equipment is particularly well suited.

Dairy and slaughter houses process equipment

In dairies the most difficult soil to remove is "burnt milk".

The milk forms gels on the inner surfaces (the surfaces that are in contact with the milk) of, e.g., heat exchangers, tanks, pipes, centrifuges, evaporators and filters.

Also coagulated milk, melted and congealed cheese and milkstone, in particular all cheese manufacturing process equipment, may be problematic to clean. All these items may be effectively cleaned by the method of the present invention.

In slaughterhouses extruderes, meat choppers and other equipment used in meat processing are difficult to clean. In meat and fish processing plants heat exchangers, cooking jars, coolers, storage tanks, pipes, centrifuges, evaporators, filters, sieves and hydrocyclones may be effectively cleaned by the method of the present invention.

Milking machines

The use of enzymes for cleaning-in-place of milking machines are advantageous too.

These machines are rather difficult to clean as they consist of many "pockets", where soil can hide. There are many rubber and plastic tubes, which are sensitive to caustic, chlorine and acids.

Today milking machines are normally cleaned automatically by use of alkaline and/or chlorine based surfactants together with sequestering agents. There is a wish in the industry to reduce the amount of chemicals in this application as they can be difficult to rinse out completely.

By enzymatic cleaning the amount of chemicals may be reduced, the amount of rinsing water may be reduced, and the chance for residual amounts of surfactants in the milk is reduced.

Membrane processes

Membrane processes are widely used in many industries today. Reverse osmosis covering ultrafiltration, nanofiltration, hyperfiltration and microfiltration are techniques used in the dairy industry and in the fermentation industry (for production of products such as enzymes and pharmaceutical products).

The spiral wounded membrane types are in general not as alkali resistant as the plate and frame systems (dependent on the polymer type in question).

Also in the brewing industry a significant penetration of membrane processes for microfiltration is expected because of the wish to get rid of kiselgur filtration. Today microfiltration is not widely used due to fouling problems and to penetration of high molecular substances into the microfiltration membrane. The soil to be removed is presumably a build up of organic complexes of hop-resin, hop-oil, β-glucans, and tannic-protein products. By choosing the most suitable carbohydrases the method of the invention may give a solution to these problems.

Enzymes

According to the invention a cleaning solution containing a protease and a lipase is preferred, but depending on the soil in question the solution may also contain other enzymes such as carbohydrases.

The amount of enzymes used in the solution varies according to the type of enzyme and the soil in question. The amount of each enzyme will typically be 0.00001–0.1% calculated as pure enzyme protein, preferably 0.001–0.01% calculated as pure enzyme protein.

Protease: Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279).

Examples of trypsin-like proteases are trypsin (e.g. of porcine or bovine origin) and the Fusarium protease described in WO 89/06270.

Examples of commercially available protease enzymes include Alcalase™, Savinase™ Esperase™ and Durazym™ products of Novo Nordisk A/S; Maxacal™, Maxapem™, Purafect™, and Purafect OXP™ products of Genencor International, and Opticlean™ and Optimase™ by Solvay Enzymes.

Lipase: Suitable lipases include those of bacterial and fungal origin. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238

023, a Candida lipase, such as a *C. antarctica* lipase, e.g., the *C. antarctica* lipase A or B described in EP 214 761, a *Pseudomonas lipase* such as a *P. alcaligenes* and *P. pseudoalcaligenes* lipase, e.g., as described in EP 218 272, a *P. cepacia* lipase, e.g., as described in EP 331 376, a Bacillus lipase, e.g., a *B. subtilis* lipase (Dartois et al., (1993), Biochemica et Biophysica acta 1131, 253–260), a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al., (1991), Gene 103, 61–67), the *Geotricum candidum* lipase (Schimada, Y. et al., (1989), J. Biochem., 106, 383–388), and various Rhizopus lipases such as a *R. delemar* lipase (Hass, M. J et al., (1991), Gene 109, 117–113), a *R. niveus* lipase (Kugimiya et al., (1992), Biosci. Biotech. Biochem. 56, 716–719) and a *R. oryzae* lipase.

Examples of commercial lipases are Lipolase™, Lipolase Ultra™, Lipomax™ and Lumafast™.

Other types of lipolytic enzymes such as cutinases may also be useful, e.g., a cutinase derived from *Pseudomonas mendocina* as described in WO 88/09367, or a cutinase derived from *Fusarium solani* pisi (e.g. described in WO 90/09446).

A phospholipase may also be used; phospholipases may be obtained from porcine or bovine pancreas or from snake or bee venom, or they may be obtained from a microorganism. Examples of commercial phospholipases are Lecitase™ available from Novo Nordisk A/S and *Streptomyces chromofuscus* phospholipase available from Toya Jozo Co., Ltd.

Carbohydrases: Depending on the polysaccharides in question to be removed one or more carbohydrases such as amylases or cellulases may be used.

Amylase: Any amylase suitable for use in alkaline solutions can be used. Suitable amylases include those of bacterial and fungal origin. Chemically or genetically modified mutants are included. Amylases include, for example, α-amylases obtained from a special strain of *B. licheniformis*, described in more detail in British Patent Specification No. 1,296,839. Particularly preferred are Termamyl™ and Duramyl™, available from Novo Nordisk A/S.

Cellulase: Any cellulase suitable for use in alkaline solutions can be used. Suitable cellulases include those of bacterial and fungal origin. Chemically or genetically modified mutants are included. Suitable cellulases are disclosed in U.S. Pat. No. 4,435,307. Particularly preferred is Celluzyme™ produced by a strain of *Humicola insolens*, available from Novo Nordisk A/S.

Cleaning-in-place

The method of the invention is particularly well suited for cleaning process equipment that prior to cleaning is soiled with a material containing proteins, fats or carbohydrates, in particular process equipment that prior to cleaning is soiled with a material containing fats and proteins.

The solution containing the enzymes is circulated through the process equipment as known in the art. The solution may contain no surfactants other than those produced from fats and proteins either in situ and/or from an earlier cleaning, or it may contain a small amount of a surfactant as described above.

The time needed for effective cleaning depends on many factors such as the process unit to be cleaned, the kind of soil, the thickness and hardness of that soil, and the temperature and pH of the solution containing the enzymes. However, a sufficient period of time will normally be from 10 minutes to 10 hours, preferably from 30 minutes to 3 hours; a sufficient temperature of the solution will typically be in the range of from 10° C. to 90° C., preferably in the range of from 20° C. to 80° C., more preferably in the range of from 40° C. to 80° C., a typical temperature will be around 50° C.; and the pH of the solution will typically be above 7, preferably be in the range of from pH 8 to pH 10.

A typical CIP-sequence according to the invention may consist of the following steps:

I: Rinse with water—Enzymatic treatment—Rinse with water.

II: Rinse with water—Enzymatic treatment—Rinse with water—Acid treatment—Rinse with water.

III: Rinse with water—Acid treatment—Rinse with water—Enzymatic treatment—Rinse with water.

IV: Enzymatic treatment—Acid treatment—optionally rinse with water.

V: Acid treatment—Enzymatic treatment—optionally rinse with water.

VI: Enzymatic treatment—Rinse with water—Acid treatment—optionally rinse with water.

VII: Acid treatment—Rinse with water—Enzymatic treatment—optionally rinse with water.

Buffers

During enzymatic hydrolysis of protein- and fat-containing material at pH>7 carboxyl groups will be nearly fully dissociated. This leads to a net release of H+ by cleaving of peptide bonds and by cleaving of ester bonds in triglyceride.

In order not to release small and volatile fatty acids (with bad smell), e.g., butyric acid in milk-fat, the pH-value is kept above 7, preferably above 8. Buffers with high capacity and/or in high concentrations (e.g. >0.1 M) may be used, or it may be preferred to use a NaOH/KOH dosing as in a pH-stat or it may be chosen to have a high pH-value from the start of the cleaning and then let the pH drop from a high value to a lower value during the cleaning.

Buffers which bind significant amounts of free Ca-ions may reduce the hydrolytic activity of some proteases and some lipases.

Examples of useful buffer systems, which may be used according to the invention, are sodiumhydrogencarbonate (pH=8) or sodiumcarbonate (pH=8–10) in which the carbonate has a concentration below 0.05 M, preferably below 0.02 M. Also potassiumsodiumhydrogenphosphate at pH=8 may be used at a concentration below 0.05 M, preferably at a concentration below 0.04 M.

The invention is further illustrated in the following examples which are not intended to be in any way limiting of the scope of the invention as claimed.

EXAMPLE 1

Total "Hydrolytic effect" (Model trials)

The total hydrolytic effect was measured as m eqvivalents of NaOH/g of dry matter by use of pH-stat at 50° C., pH=8.0 on the basis of a 0.4% suspension of burnt whole milk powder. After addition of 0.025% Esperase 8.0 L (available from Novo Nordisk A/S) and/or 0.025% Lipolase 100 L (available from Novo Nordisk A/S) the hydrolysis lasted for 30 minutes whereafter the amount of NaOH was measured. The data are presented in Table 1:

TABLE 1

Data for hydrolytic effect on burnt whole milk
(120° C. for 30 minutes):

| Conc. of Esperase 8.0 L (% w/w) | Conc. of Lipolase 100 L (% w/w) | m eqv. NaOH/g of dry matter |
|---|---|---|
| 0.025 | 0 | 0.23 |
| 0 | 0.025 | 0.12 |
| 0.025 | 0.025 | 0.55 |

It can be seen from Table 1 that there is a significant synergistic effect of combining the protease and the lipase.

EXAMPLE 2
CIP of Heat Exchanger Plates

In pilot plant a cleaning-in-place of a plate heat exchanger used for high pasteurization of whole milk for 6 hours was demonstrated. The heat exchanger had a 2–3 mm layer of burnt milk. A circulation of a solution containing 0.1% Esperase 8.0 L and 0.1% Lipolase 100 L, 2.0 g NaOH/l and 6.8 g $KH_2PO_4$/l (pH=8), 50° C. for 2 hours was used (both enzymes available from Novo Nordisk A/S). After this treatment the exchanger was clean. No other detergents than those produced in situ during the cleaning was applied. This proves that the enzymes form soap and emulsifier from the degraded soil. In this test no acid treatment following the enzyme treatment was necessary.

EXAMPLE 3
CIP of Heat Exchanger Plates

A complete CIP-programme was carried out on heat exchanger plates that were heavily soiled after high pasteurization of whole milk for 6 hours. The heat exchanger was rinsed in 50° C. hot water for 10 minutes. Hereafter an enzyme treatment using 0.1% Esperase 8.0 L and 0.1% Lipolase 100 L, 2.0 g NaOH/l and 6.8 g $KH_2PO_4$/l (pH=8), 50° C. for 60 minutes was carried out (both enzymes available from Novo Nordisk A/S). A rinsing was carried out for 5 minutes using 50° C. hot water. A 30 minutes treatment using 0.5% $HNO_3$ was made. Finally the heat exchanger plates were clean. It should be noted that in this Example an acid treatment was necessary due to a shorter enzyme treatment (60 minutes) compared with Example 2 in which the enzyme treatment lasted 2 hours.

EXAMPLE 4
CIP of Heat Exchanger Plates

A complete CIP-programme was carried out on heat exchanger plates that were heavily soiled after high pasteurization of whole milk for 6 hours. The heat exchanger was rinsed in 50° C. hot water for 10 minutes. Hereafter a treatment using 0.5% $HNO_3$ for 30 minutes at 50° C. was made. The acid was rinsed out with water and an enzyme treatment using 0.1% Esperase 8.0 L and 0.1% Lipolase 100 L, 2.0 g NaOH/l and 6.8 g KH2PO4/l (pH=8), 50° C. for 60 minutes was carried out (both enzymes available from Novo Nordisk A/S). A final rinsing was carried out for 5 minutes using 50° C. hot water. The heat exchanger was clean.

The cleaning result achieved in Example 4 gave the same result as the cleaning result achieved in Example 3.

EXAMPLE 5
Milking machines

The aim of cleaning milking machines was that the hydrolytic effect of the enzymes (protease+lipase) should match that of alkali (NaOH).

We have seen a surprising significant synergistic effect of protease and lipase for the hydrolysis of whole milk. The hydrolytic effect on a cost equivalent dosage of 0.025% Esperase 8.0 L+0.025% Lipolase 100 L (both enzymes available from Novo Nordisk A/S) at pH=8 seems to be equivalent to 0.32 g NaOH/l (pH=11.2).

EXAMPLE 6
CIP of Heat Exchanger Plates

A complete CIP-programme was carried out on heat exchanger plates that were heavily soiled after high pasteurization of raw unhomogenized whole milk for 6 hours. The heat exchanger was rinsed in 50° C. hot water for 10 minutes. Hereafter an enzyme treatment using 0.1% Esperase 8.0 L and 0.1% Lipolase 100 L, +0.025% Dobanol 25-7 from Shell A/S and 0.025 M $NaHCO_3$ (pH=8), 50° C. for 60 minutes was carried out (both enzymes available from Novo Nordisk A/S). A rinsing was carried out for 5 minutes using 50° C. hot water. A 15 minutes treatment using 0.5% $HNO_3$ was made. Finally the heat exchanger plates were clean.

EXAMPLE 7
Total "Hydrolytic effect"

The total hydrolytic effect was measured on unhomogenized/pasteurized whole milk (Table 2) and on homogenized/pasteurized whole milk (Table 3) as m eqv NaOH/g of dry matter by use of pH-stat at 50° C., pH=8.0 on the basis of a 0.4% suspension of milk. After addition of Esperase 8.0 L and/or Lipolase 100 L (both enzymes available from Novo Nordisk A/S) the hydrolysis lasted for 30 minutes whereafter the amount of NaOH was measured.

TABLE 2

Data for hydrolytic effect on unhomogenized whole milk,
S = 0.4% of dry matter, pH 8.0:

| Conc. of Esperase 8.0 L (% w/w) | Conc. of Lipolase 100 L (% w/w) | m eqv. NaOH/g of dry matter |
|---|---|---|
| 0.025 | 0 | 0.24 |
| 0 | 0.025 | 0.07 |
| 0.025 | 0.025 | 0.84 |

TABLE 3

Data for hydrolytic effect on unhomogenized whole milk,
S = 0.4% of dry matter, pH 8.0:

| Conc. of Esperase 8.0 L (% w/w) | Conc. of Lipolase 100 L (% w/w) | m eqv. NaOH/g of dry matter |
|---|---|---|
| 0.025 | 0 | 0.25 |
| 0 | 0.025 | 0.18 |
| 0.025 | 0.025 | 0.88 |

It was additionally tried to add different concentrations of SDS (Sodium-dodecylsulphate) to the enzyme solutions but there was no effect calculated as (m eqv. NaOH/g of dry matter) whether or not SDS was added.

Different proteases (Esperase 8.0 L, Alcalase 2.5 L and Savinase 16 L, all available from Novo Nordisk A/S) were also tested giving the following results:

TABLE 4

Data for hydrolytic effect on unhomogenized whole milk,
S = 0.4% of dry matter, pH 8.0.
Effect of different proteases:

| Conc. of protease (% w/w) | Conc. of Lipolase (% w/w) | m eqv. NaOH/g of dry matter |
|---|---|---|
| 0.025 (Esperase) | 0.025 | 0.85 |
| 0.025 (Esperase) | 0.025 | 1.05 |
| 0.025 (Esperase) | 0.025 | 0.95 |

It can be seen from Table 4 that all three proteases perform fine.

EXAMPLE 8

Viscosity measurements

The viscosity was measured on diluted solutions (0.4% and 0.8%) of unhomogenized milk by use of a Hoebbler viscosimeter at 25° C. The milk was tested alone, after addition of 0.025% Esperase 8.0 L+0.025% Lipolase 100 L, and after addition of 2.5 g NaOH/l. The results are presented below:

| Product: | Treatment: | Kinematic viscosity: |
|---|---|---|
| Milk (0.4% DM) | | 0.965 mPa X S |
| Milk (0.8% DM) | | 0.990 mPa X S |
| Milk (0.4% DM) | 0.025% E* + L* | 0.968 mPa X S |
| Milk (0.8% DM) | 0.025% E* + L* | 1.001 mPa X S |
| Milk (0.4% DM) | 2.50 g NaOH/l | 0.997 mPa X S |
| Milk (0.8% DM) | 2.50 g NaOH/l | 1.020 mPa X S |
| 2.50 g NaOH/l | | 0.955 mPa X S | wherein E* means Esperase 8.0 L, and L* means Lipolase 100 L.

It can be seen from the results presented above that the enzyme containing solutions have a lower viscosity than the solutions with NaOH. The rinsing after enzyme treatment may therefore be more efficient.

EXAMPLE 9

Ultrafiltration

A plate and frame module DDS type 10 having 336 cm² membrane type GR 61PP, DDS, was used for the trials. The nominal water flux was according to the data sheet: 250–350 l/m2/h at 20° C., 4 Bar. This is recalculated to 17° C. and 3.1 Bar (Avg) corresponding to 175–250 l/m²/h.

On a new and clean membrane the water flux was measured at the following parameters: Temp. 17° C., P (avg.)=3.1 Bar, corresponding to around 67 ml/min, which is eqvialent to 120 l/m²/h +/− 10%. This flux should be obtained on a membrane after cleaning.

In all cases the membranes were soiled by ultrafiltration of 2 liter whole milk at 50° C. minutes to approximately 25% dry matter (refraktometer).

| Trial no. | NaOH | Cleaning system I. Esperase 8.0 L | Cleaning system I. Lipolase 100 L | Temp. ° C. | Cleaning system II. % HNO₃ |
|---|---|---|---|---|---|
| 6 | | 0.025% | 0.025% | 50 | 0.125 |
| 7 | | 0.025% | | 50 | 0.125 |
| 8 | | | 0.025% | 50 | 0.125 |
| 9 | 2.5 g/L | | | 50 | 0.125 |
| 10 | 2.5 g/L | | | 75 | 0.125 |

Procedure:

1. The membranes were soiled by ultrafiltration of 2 liter whole milk at 50° C. for 120 minutes to approximately 25% dry matter (refraktometer) using an inlet pressure of 3.2 Bar and an outlet pressure of 3.0 Bar. The flow through the pump was 3.5–4 liter per minutes.

2. The circulation vessel was rinsed with water at 50° C. When it was clean the water was flowed through the module at no back pressure. This secures maximal flow through the module. This rinsing was carried out for 5 minutes. Hereafter the flux and the temperature were measured. The corrigated flux was then calculated.

3. Water having a temperature of 50° C. was added. $Na_2CO_3$ was then added to a concentration of 0.01 molar. pH was adjusted to 8.0 by use of 1 N HCl. Hereafter the cleaning agents (enzymes or NaOH) were added.

4. Recirculation was initiated. Also the permeate was recirculated to the vessel. Recirculation was carried out for 60 minutes at 50° C. by low pressure (means maximal flow). The flux and temperature were measured for control purposes during the cleaning operation.

5. A cleaning was now made with the $HNO_3$ solution mentioned in the work plan. Recirculation was initiated. Also here the permeate was recirculated to the vessel. Recirculation was carried out for 5 minutes at 25° C. by low pressure (means maximal flow). The flux and temperature were measured for control purposes during the cleaning operation.

6. Finally the content was rinsed out of the vessel and cold water was added. After 5 minutes recirculation the water flux was measured at an average pressure at 3.1 Bar and the corrigated flux was calculated. This flux was the finally obtainable flux after the cleaning operation.

The results are shown below in Table 5.

It can be seen from Table S that the flux is only at the starting level (120 l/m²/h +/− 10%) after treatment with a protease +lipase solution (see trial no. 6 in Table 5).

TABLE 5

| Trial no. | Final concentration, % DM after 120 min. | Flux before cleaning l/h/m², corr. | Cleaning system I. | Flux after cleaning I l/h/m², corr. | Cleaning system. II. | Flux after cleaning II l/h/m², corr. |
|---|---|---|---|---|---|---|
| 9 | 27.0 | 17.5 | NaOH: 0.25%, (Maximal flow) 50° C., 60 min. | 50.6 | 0.125% w/w HNO₃ (Maximal flow) | 46.9 |
| 10 | 30.5 | 15.6 | NaOH: 0.25%, (Maximal flow) 75° C., 60 min. | 61.2 | 0.125% w/w HNO₃ (Maximal flow) | 48.3 |
| 6 | 25.0 | 10.2 | Lipolase: 0.025% Esperase: 0.025% (Maximal flow) | 69.9 | 0.125% w/w HNO₃ (Maximal flow) | 108.5 |
| 7 | 29.30 | 13.5 | Esperase: 0.025% (Maximal flow) | 23.9 | 0.125% w/w HNO₃ (Maximal flow) | 47.5 |
| 8 | 20.2 | 11.8 | Lipolase: 0.025% (Maximal flow) | 18.9 | 0.125% w/w HNO₃ (Maximal flow) | 45.3 |

What is claimed is:

1. A method of cleaning-in-place process equipment soiled with a material containing fats and proteins comprising contacting a surface of the equipment soiled with fats and proteins with a solution consisting essentially of a 0.00001% to 0.1% of a protease enzyme calculated as pure enzyme protein, and 0.00001% to 0.1% of a lipase enzyme calculated as pure enzyme protein, for a sufficient period of time to substantially remove the soiled fat and protein material.

2. The method of claim 1, wherein the process equipment is selected from the group consisting of heat exchangers, tanks, pipes, centrifuges, evaporators, filters, extruders, meat choppers, cooking jars, coolers, storage tanks, sieves, hydroclones, ultrafiltration units, nanofiltration units, hyperfiltration units, microfiltration units and milking machines.

3. The method of claim 1, wherein the process equipment is a dairy or a slaughter house process equipment.

4. The method of claim 1, wherein the protease is a serine protease.

5. The method of claim 4, wherein the protease is a subtilisin.

6. The method of claim 4, wherein the protease is trypsin or the protease is obtained from Fusarium.

7. The method of claim 1, wherein the lipase is obtained from one of Humicola, Mucor or Pseudomonas.

8. The method of claim 1, wherein the soiled equipment is contacted with the solution for a period of time from 10 minutes to 10 hours.

9. The method of claim 1, wherein the solution has a pH above 7.

10. The method of claim 5, wherein the protease is a Bacillus subtilisin selected from the group consisting of subtilisin Carlsberg, BPN', subtilisin 309, subtilisin 147, and subtilisin 168.

11. The method of claim 9, wherein the soiled equipment is contacted with the solution for a period of time from 30 minutes to 3 hours.

12. The method of claim 10, wherein the solution has a pH of between 8 and 10.

* * * * *